(12) United States Patent
Di Luccio et al.

(10) Patent No.: US 7,687,681 B2
(45) Date of Patent: Mar. 30, 2010

(54) MENSES SPECIFIC ABSORBENT SYSTEMS

(75) Inventors: Robert Cosmo Di Luccio, Titusville, FL (US); Michael Allen Daley, Alpharetta, GA (US); David Charles Potts, Dunwoody, GA (US); Gregory Marc Lefkowitz, Atlanta, GA (US); Jack Nelson Lindon, Alpharetta, GA (US); David Martin Jackson, Roswell, GA (US); Matthew David Young, Kennesaw, GA (US); Cheryl Ann Mocadlo, New London, WI (US); Candace Dyan Krautkramer, Neenah, WI (US)

(73) Assignee: Kimberly-Clark Worldwide, Inc., Neenah, WI (US)

(*) Notice: Subject to any disclaimer, the term of this patent is extended or adjusted under 35 U.S.C. 154(b) by 1007 days.

(21) Appl. No.: 09/859,665

(22) Filed: May 18, 2001

(65) Prior Publication Data

US 2002/0040210 A1    Apr. 4, 2002

Related U.S. Application Data

(60) Provisional application No. 60/207,512, filed on May 26, 2000, provisional application No. 60/207,513, filed on May 26, 2000.

(51) Int. Cl.
*A61F 13/15* (2006.01)

(52) U.S. Cl. ............... 604/368; 604/360; 604/375; 604/385.04

(58) Field of Classification Search ............ 604/365, 604/368, 375, 378, 385.04–385.05, 385.25–385.28, 604/385.101, 380, 360
See application file for complete search history.

(56) References Cited

U.S. PATENT DOCUMENTS

| 3,338,992 | A | 8/1967 | Kinney |
| 3,341,394 | A | 9/1967 | Kinney |
| 3,423,266 | A | 1/1969 | Davies et al. |
| 3,502,763 | A | 3/1970 | Hartmann |
| 3,542,615 | A | 11/1970 | Dobo et al. |
| 3,692,618 | A | 9/1972 | Dorschner et al. |
| 3,802,817 | A | 4/1974 | Matsuki et al. |
| 3,849,241 | A | 11/1974 | Butin et al. |

(Continued)

FOREIGN PATENT DOCUMENTS

EP    019 371    11/1980

(Continued)

OTHER PUBLICATIONS

Manson, John A. and Sperling, Leslie H., *Polymer Blends & Composites*, Plenum Press, a division of Plenum Publishing Corp., New York, New York, pp. 273-277 (1976).

*Primary Examiner*—Tatyana Zalukaeva
*Assistant Examiner*—Lynne Anderson
(74) *Attorney, Agent, or Firm*—Dority & Manning, P.A.

(57) ABSTRACT

A personal care absorbent article such as a disposable diaper, sanitary pad or tampon, wound dressing or bandage which includes a nonwoven web material made from a plurality of polymeric fibers having at least one treatment chemistry suitable for modifying at least one characteristic of a high viscoelasticity fluid upon contact with the high viscoelasticity fluid. In accordance with one particularly preferred embodiment, the treatment chemistry is suitable for immobilizing the high viscoelasticity fluid within the nonwoven web material.

29 Claims, 6 Drawing Sheets

U.S. PATENT DOCUMENTS

| | | | |
|---|---|---|---|
| 4,340,563 A | 7/1982 | Appel et al. | |
| 4,363,322 A * | 12/1982 | Andersson | 604/359 |
| 4,753,834 A | 6/1988 | Braun et al. | |
| 4,790,836 A * | 12/1988 | Brecher | 604/359 |
| 4,795,668 A | 1/1989 | Krueger et al. | |
| 4,959,060 A * | 9/1990 | Shimomura et al. | 604/368 |
| 5,057,368 A | 10/1991 | Largman et al. | |
| 5,069,970 A | 12/1991 | Largman et al. | |
| 5,108,820 A | 4/1992 | Kaneko et al. | |
| 5,108,827 A | 4/1992 | Gessner | |
| 5,112,690 A | 5/1992 | Cohen et al. | |
| 5,209,966 A | 5/1993 | Lange et al. | |
| 5,212,270 A | 5/1993 | Lal | |
| 5,219,644 A | 6/1993 | Lal et al. | |
| 5,277,976 A | 1/1994 | Hogle et al. | |
| 5,324,561 A | 6/1994 | Rezai et al. | 428/72 |
| 5,336,552 A | 8/1994 | Strack et al. | |
| 5,342,333 A * | 8/1994 | Tanzer et al. | 604/359 |
| 5,364,380 A * | 11/1994 | Tanzer et al. | 604/359 |
| 5,382,400 A | 1/1995 | Pike et al. | |
| 5,466,410 A | 11/1995 | Hills | |
| 5,506,035 A * | 4/1996 | Van Phan et al. | 428/196 |
| 5,527,534 A | 6/1996 | Myhling | |
| 5,540,992 A | 7/1996 | Marcher et al. | |
| 5,658,582 A * | 8/1997 | Dorigatti et al. | 424/402 |
| 5,728,081 A * | 3/1998 | Baer et al. | 604/370 |
| 5,759,569 A * | 6/1998 | Hird et al. | 424/443 |
| 5,782,819 A * | 7/1998 | Tanzer et al. | 604/385.04 |
| 5,990,377 A * | 11/1999 | Chen et al. | 604/381 |
| 6,060,636 A | 5/2000 | Yahiaoui et al. | |
| 6,080,908 A * | 6/2000 | Guarracino et al. | 604/359 |
| 6,159,591 A * | 12/2000 | Beihoffer et al. | 428/327 |
| 6,177,607 B1 * | 1/2001 | Blaney et al. | 604/378 |
| 6,245,693 B1 * | 6/2001 | Gagliardi et al. | 442/76 |
| 6,350,711 B1 * | 2/2002 | Potts et al. | 442/123 |
| 6,479,728 B1 * | 11/2002 | DiPalma | 604/378 |
| 6,562,192 B1 * | 5/2003 | Hamilton et al. | 162/56 |

FOREIGN PATENT DOCUMENTS

| | | |
|---|---|---|
| EP | 793 971 | 9/1997 |
| GB | 2 274 650 | 8/1994 |
| WO | WO 00/00228 | 1/2000 |
| WO | WO 00/25835 | 5/2000 |
| WO | WO/ 01/45757 | 6/2001 |

* cited by examiner

MENSES SPECIFIC ABSORBENT SYSTEMS

CROSS-REFERENCE TO RELATED APPLICATIONS

This application claims the benefit of provisional U.S. patent application Ser. No. 60/207,512 filed 26 May 2000 and U.S. provisional patent application Ser. No. 60/207,513 filed 26 May 2000.

FIELD OF THE INVENTION

This invention relates to treatment chemicals and systems which are capable of altering the properties of high viscosity materials including, but not limited to, bodily exudates such as menstrual fluid, blood and fecal matter, and disposable absorbent articles such as disposable diapers, training pants, incontinence garments, feminine hygiene products including sanitary pads and tampons, bandages, wound dressings, wipes and the like employing such treatment chemicals and systems. These articles typically employ polymeric fibers which may be formed into nonwoven fabrics, textiles or batts and the like. In addition, this invention relates to means for incorporating such treatment chemicals and systems into an absorbent material and arranging for its use in the disposable absorbent articles so as to provide discrete functions such as fluid intake, distribution, retention or shaping, or to provide multiple functions such as fluid intake/distribution or fluid intake/distribution/retention.

BACKGROUND OF THE INVENTION

Fibrous materials used to deliver widely varying agents are well known and readily available for many purposes. Examples include wet wipes, disinfecting bandages and cleaning implements, and personal care absorbent articles such as disposable diapers, sanitary pads and tampons and the like.

In addition, the incorporation of additives such as surfactants into the fibrous materials to enhance control of absorbed fluids is also known. A nonwoven web material with improved softness comprising monofilaments or fibers of a thermoplastic material to which a wetting agent such as cationic, anionic, and nonionic surfactants are added is taught by U.S. Pat. No. 4,753,834 to Braun et al. U.S. Pat. No. 5,112, 690 to Cohen et al. teaches a method of treating a low hydrohead fibrous porous web material to increase its retentive wettability in which a surface active agent having a hydrophile-lipophile balance of at least about six is adhered to the low hydrohead fibrous porous web material and a corona discharge equivalent to a charge of at least about 0.6 watt minute per square foot per side of the web material is applied to the surface active agent bearing web material. Treated polymer fabrics having improved wicking/wetting characteristics comprising a hydrophobic polymer fabric treated with a wetting agent are taught by U.S. Pat. No. 5,209,966 to Lange et al., U.S. Pat. No. 5,212,270 to Lal, and U.S. Pat. No. 5,219,644 to Lal et al. U.S. Pat. No. 5,527,534 to Myhling teaches a sponge capable of delivering an active pharmaceutical agent into the vaginal canal during insertion of the sponge, while the sponge is resident in the vagina and during removal from the vagina, wherein the sponge is a polyurethane foam in which a non-ionic surfactant, such as Pluronic F68 is used in the polyurethane formulation to provide uniform desired cell structure, density, tensile strength, porosity, and degree of hydrophilicity. For menses and other blood-containing fluids, increases in surface wettability upon fluid contact is a major problem. This is due to protein deposition which occurs on virtually all materials, even highly hydrophobic surfaces such as TEFLON®. The only surfaces that have been shown to completely block protein absorption are surfaces with covalently attached polyethylene oxide molecules. These surfaces are highly wettable, however, and would promote fluid attachment and staining, even without protein binding.

Accordingly, there is a need for treatment chemistries and systems which are capable of altering the properties of high viscosity materials in a predefined manner, and there is a need for means for incorporating such treatment chemistries and systems into fibrous nonwoven materials.

SUMMARY OF THE INVENTION

It is one object of this invention to provide a nonwoven web material with at least one treatment chemistry which is capable of altering the properties of high viscosity materials in a predefined manner.

It is another object of this invention to provide personal care absorbent articles with at least one treatment chemistry which is capable of altering the properties of high viscosity materials so as to enhance the performance and functionality of the personal care absorbent articles. Altering the properties of high viscosity materials in accordance with this invention refers to changes in, for example, viscosity, component cellular structure, and composition.

These and other objects of this invention are addressed by a personal care absorbent article comprising a nonwoven web material comprising a plurality of polymeric fibers and comprising at least one treatment chemistry suitable for modifying at least one property of a high viscoelasticity fluid upon contact with the high viscoelasticity fluid. The treatment chemistries may be disposed in the interior of the polymeric fibers, on the surface of the polymeric fibers or within the nonwoven web material, such as in the interstices formed by the polymeric fibers. It will be apparent that numerous dispositions of the treatment chemistries as well as disposition of the fibers comprising the treatment chemistries within the nonwoven web material, depending upon the objective of the placement within the nonwoven web material, are possible. Thus, the polymeric fibers may be multicomponent fibers in which the treatment chemistries are disposed in fewer than all of the components comprising the multicomponent fibers. And/or the treated polymeric fibers may be disposed throughout the nonwoven web material or within zones of the nonwoven web material depending upon the application of the nonwoven web material. And, still further, in the case of multilayer nonwoven web materials, the treatment chemistries may be disposed in polymeric fibers comprising fewer than all of the layers comprising the multilayer material.

Nonwoven web materials of this invention include, but are not limited in any way to, spunbond materials, meltblown materials, bonded carded web materials, air laid materials, bonded and unbonded pulp materials, coform materials, fibrous materials such as fluff and combinations thereof, for example, multilayer materials and laminates.

The objects of this invention are also addressed by a method for treating viscoelastic fluid whereby management of the viscoelastic fluid by an absorbent article is improved in which at least one portion of the absorbent article is treated with a treatment chemistry suitable for altering at least one property of the viscoelastic fluid after which the absorbent article is contacted with the viscoelastic fluid, thereby altering at least one property of the viscoelastic fluid or the interaction of the viscoelastic fluid with the absorbent article. For example, rather than altering the viscoelastic fluid, the treatment chemistry may alter the surface properties of the absorbent article as the viscoelastic fluid is absorbed by the absorbent article or it may combine with the viscoelastic fluid to form another composition, such as a coating on portions of the absorbent article.

Suitable treatment chemistries for use in the nonwoven web materials of this invention include gelling agents, which typically are used to increase the viscosity or elasticity of a fluid, mucolytic agents, which typically are used to decrease the viscosity or elasticity of a fluid, agglutinizing agents, which typically are used to alter the physical state of red blood cells, lysing agents, which typically are used to break apart red blood cells and plasma precipitators, which typically are used for rapid precipitation of blood plasma proteins.

BRIEF DESCRIPTION OF THE DRAWINGS

These and other objects and features of this invention will be better understood from the following detailed description taken in conjunction with the drawings, wherein.

DESCRIPTION OF PREFERRED EMBODIMENTS

Figure 1:
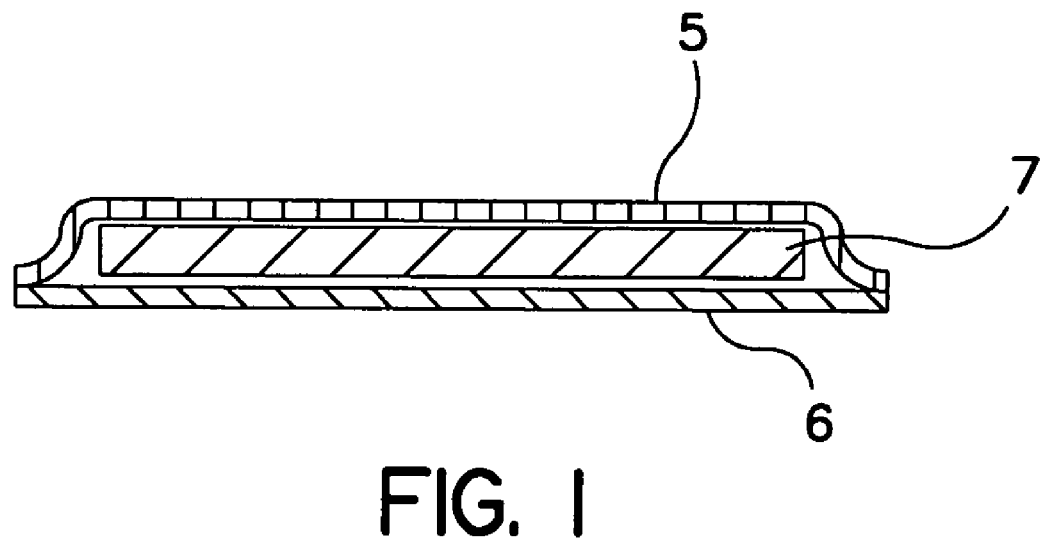
FIG. 1 is a cross-sectional view of a typical personal care absorbent article.

While this invention will be described in connection with preferred and other embodiments, it will be understood that it is not intended to limit the invention to those embodiments. On the contrary, it is intended to cover all alternatives, modifications and equivalents as may be included within the spirit and scope of the invention as defined by the appended claims.

Definitions

As used herein, the term "comprising" is open and includes not only recited elements, components or steps, but also any additional elements, components or steps that do not prevent operation of the invention as described.

As used herein, the term "nonwoven web" or "nonwoven material" means a material having a structure of individual fibers or threads which are interlaid, but not in an identifiable manner, as in a knitted fabric. Nonwoven materials or webs have been formed from many processes such as, for example, spunbonding processes, meltblowing processes, and bonded carded web processes. The basis weight of nonwoven fabrics is usually expressed in grams per square meter (gsm) and the fiber diameters are usually expressed in microns.

As used herein, the term "spunbond fibers" refers to small diameter fibers which are formed by extruding molten thermoplastic material as filaments from a plurality of fine, usually circular capillaries of a spinneret, with the diameter of the extruded filaments then being rapidly reduced as by, for example, in U.S. Pat. No. 4,340,563 to Appel et al., U.S. Pat. No. 3,692,618 to Dorschner et al., U.S. Pat. No. 3,802,817 to Matsuki et al., U.S. Pat. No. 3,338,992 and 3,341,394 to Kinney, U.S. Pat. No. 3,502,763 to Hartmann, and U.S. Pat. No. 3,542,615 to Dobo et al. Spunbond fibers are generally not tacky when they are deposited onto a collecting surface. Spunbond fibers are generally continuous and have average diameters (from a sample of at least 10) larger than 7 microns, more particularly, between about 10 and 50 microns. The fibers may also have shapes such as those described in U.S. Pat. No. 5,277,976 to Hogle et al., U.S. Pat. No. 5,466,410 to Hills, and U.S. Pat. No. 5,069,970 and U.S. Pat. No. 5,057,368 to Largman et al., which describe hybrids with unconventional shapes. A nonwoven web of spunbond fibers produced by melt spinning is referred to as a "spunbond".

As used herein, the term "meltblowing" refers to a process in which fibers are formed by extruding a molten thermoplastic material through a plurality of fine, usually circular, die capillaries as molten threads or filaments into converging high velocity, usually heated, gas (for example air) streams which attenuate the filaments of molten thermoplastic material to reduce their diameter, which may be to microfiber diameter. Thereafter, the meltblown fibers are carried by the high velocity gas stream and are deposited on a collecting surface, often while still tacky, to form a web of randomly dispersed meltblown fibers. Such a process is disclosed, for example, by U.S. Pat. No. 3,849,241 to Butin. Meltblown fibers are microfibers which may be continuous or discontinuous and are generally smaller than 10 microns in average diameter.

As used herein, the term "polymer" generally includes, but is not limited to, homopolymers, copolymers, such as for example, block, graft, random and alternating copolymers, terpolymers, etc., and blends and modifications thereof. In addition, unless otherwise specifically limited, the term "polymer" includes all possible geometric configurations of the material. The configurations include, but are not limited to, isotactic, atactic, syndiotactic, and random symmetries.

As used herein, the term "monocomponent" fiber refers to a fiber formed from one or more extruders using only one polymer. This is not meant to exclude fibers formed from one polymer to which small amounts of additives have been added for coloration, anti-static properties, lubrication, hydrophilicity, etc. These additives, for example titanium dioxide for coloration, are generally present in an amount less than about 5 weight percent and more typically about 2 weight percent.

As used herein, the term "bicomponent fibers" refers to fibers which have been formed from at least two different polymers extruded from separate extruders but spun together to form one fiber. Bicomponent fibers are also sometimes referred to as conjugate fibers or multicomponent fibers. The polymers are arranged in substantially constantly positioned distinct zones across the cross-section of the bicomponent fibers and extend continuously along the length of the bicomponent fibers. The configuration of such a bicomponent fiber may be, for example, a sheath/core arrangement wherein one polymer is surrounded by another, or may be a side-by-side arrangement, a pie arrangement, or an "islands-in-the-sea" arrangement. Bicomponent fibers are taught by U.S. Pat. No. 5,108,820 to Kaneko et al., U.S. Pat. No. 4,795,668 to Krueger, et al., U.S. Pat. No. 5,540,992 to Marcher et al., and U.S. Pat. No. 5,336,552 to Strack et al. Bicomponent fibers are also taught by U.S. Pat. No. 5,382,400 to Pike et al., and may be used to produce crimp in the fibers by using the differential rates of expansion and contraction of the two (or more) polymers. For two component fibers, the polymers are desirably present in ratios of 75/25 to 25/75 or any other desired ratio and, as an example, may be 50/50. Fibers formed of two or more segments of the same polymer, such as a polypropylene (PP)/PP fiber are considered to be monocomponent fibers.

As used herein, the term "biconstituent fibers" refers to fibers which have been formed from at least two polymers extruded from the same extruder as a blend. The term "blend" is defined below. Biconstituent fibers do not have the various polymer components arranged in relatively constantly positioned distinct zones across the cross-sectional area of the fiber and the various polymers are usually not continuous along the entire length of the fiber, instead usually forming fibrils which start and end at random. Biconstituent fibers are sometimes also referred to as multiconstituent fibers. Fibers of this general type are discussed in, for example, U.S. Pat. No. 5,108,827 to Gessner. Bicomponent and biconstituent fibers are also discussed in the textbook *Polymer Blends and Composites* by John A. Manson and Leslie H. Sperling, copyright 1976 by Plenum Press, a division of Plenum Publishing Corporation, New York, N.Y., IBSN 0-306-30831-2, at pages 273 through 277.

As used herein, the term "personal care absorbent article" means disposable diapers, training pants, absorbent underpants, adult incontinence products, feminine hygiene products, including sanitary pads and tampons, bandages, wound dressings, wipes, and the like.

As used herein, the term "treatment chemistry" refers to a compound or composition that is capable of forming, by itself or in combination as a blend or mixture with another compound or composition as an agend, an extrudable melt component of a multicomponent fiber, or a compound that can be suspended in the spin dope of one or more polymers in a wet or dry spinning process and thereafter being activated to produce an intended affect under intended use conditions. Also, the term refers to a compound or composition which may be applied onto the surface of an absorbent article, onto the surface of one or more elements of an absorbent article or within the interior of the absorbent article, but external to the components, such as polymeric fibers, employed in producing the absorbent article or elements of the absorbent article. In addition, in combination with a positive displacement carrier, the treatment chemistries are capable under use conditions of blooming or diffusing to the surface of the multicomponent fiber in an amount and within a time required to achieve the intended result.

As used herein, the term "positive displacement carrier" means a compound or composition that, when combined with a treatment chemistry under conditions of use, will cause the treatment chemistry to be dispensed by, for example, diffusing or blooming from the combination at a desired rate.

As used herein, the term "agend" means a composition containing a treatment chemistry and a positive displacement carrier that may, either by itself, or in combination with another component be formed into a fiber by any one or more of the above-described processes. Thus, the agend may form a monocomponent fiber, a multicomponent fiber with one or more other components, or a biconstituent fiber, for example. The amount of treatment chemistry in an agend will depend on the chemistry and the intended use, and the additional positive displacement carrier of the agend will be determined by these factors as well as the ability of the composition as a whole to release the treatment chemistry in a controlled manner.

As used herein, the term "intake" refers to the ability of an absorbent article to absorb fluid. Intake time is used to assess the quality of absorption with lower intake times denoting materials capable of rapid absorption and higher intake times denoting materials with poorer absorption.

As used herein, the term "proteinaceous fluids" refers to a fluid that contains protein or protein breakdown products such as blood or menses. For purposes of evaluation of the material treatment system of this invention, a menstrual simulant, the preparation of which is discussed hereinbelow, was utilized which has similar properties to menstrual discharge.

As used herein, the term "high viscoelasticity material" refers to a material having a viscosity greater than about 0.1 poise and/or an elasticity greater than about 0.02 poise. Included within the scope of this term are menstrual fluids, blood and runny fecal matter.

"High viscoelastic simulant" or "menses simulant" is a material which simulates the viscoelastic and other properties of menses. The first step in preparing a high viscoelastic biological simulant is to prepare 120 mL of ovomucin by separating the yolk and egg whites of about one dozen large eggs, saving the egg white and removing the white strand of egg white. The egg whites are filtered one time using a 2 mm nylon mesh by placing the egg whites on the filter and allowing them to set on the mesh for 5 minutes while gently moving the egg white on the filter. 120 ml of thick egg white is then placed in a 300 ml transfer bag followed by the addition of 80 ml of plasma into the 300 ml transfer bag and gentle mixing of the solution by hand until it looks fairly homogeneous. The solution is placed into a Stomacher mixer (Stomacher 400 Laboratory Blender, Seward Medical, London SE1 1PP UK) at a low setting for 60 seconds. From there, the mixture is placed into a dialysis bag having dialysis clips on each end in a manner which minimizes the amount of air in the bag. Preferably no air should be in the bag. (It should be noted that to open the dialysis bag, the dialysis bag needs to be immersed in distilled water for 1 minute.) The filled bag is weighed (initial wt.), placed into a trough with Superabsorbent Polymer (Favor 880 Stockhausen, Inc. 2401 Doyle Street Greensboro, N.C. 27406) covering the bag on all sides and refrigerated for 6 hours. Thereafter, the superabsorbent with water is rinsed off and the bag dried thoroughly. The bag is reweighed (weight loss is typically about 46-50 grams), and the volume of fluid after dialysis is measured using a 60 cc syringe. Next, swine blood is centrifuged at 3000 rpm, 20° C. for 30 minutes. The plasma is separated from red blood cells with a disposable pipette. The red blood cells are saved and a 70% mixture of ovomucin/plasma and 30% red blood cells is made. The mixture is gently mixed on a magnetic plate and the resulting solution put into a transfer bag (marking down the volume). Using a syringe, excess air in the bag is removed and the mixture manually gently mixed for 5 minutes. The mixture is then refrigerated for 24 hours before use.

To use the simulant for testing, it is warmed for 10 minutes at 22° C. in a water bath before testing. The simulant is manually mixed in the bag for 4 minutes (no visual separation should be seen), the amount needed for testing removed and placed in a beaker. The simulant is then mixed using a magnetic stirrer (on lowest setting) for 5 minutes.

"Low viscoelastic simulant" or "menses simulant" is another material which simulates the viscoelastic and other properties of menses. To prepare the fluid, blood, such as defibrinated swine blood, is separated by centrifuge at 3000 rpm for 30 minutes, although other methods or speeds and times may be used if effective. The plasma is separated and stored separately, the buffy coat removed and discarded, and the packed red blood cells stored separately as well. Eggs, such as jumbo chicken eggs, are separated, the yoke and chalazae discarded, and the egg white retained. The egg white is separated into thick and thin portions by straining the white through a 1000 micron nylon mesh for about three minutes, and the thinner portion discarded. Alternative mesh sizes may be used, and the time or method may be varied provided the viscosity is at least that required. The thick portion of egg white which was retained on the mesh is collected and drawn into 60 cc syringes which are then placed on a programmable syringe pump and the fluid homogenized by expelling and refilling the contents five times. In our case, the amount of homogenization was controlled by the syringe pump rate of about 100 ml/min, and the tubing inside diameter of about 0.12 inches. After homogenizing, the thick egg white has a viscosity of about 20 centipoise at 150 sec-1 and it is then centrifuged to remove debris and air bubbles. After centrifuging, 80 mL of the thick homogenized egg white, which contains ovomucin, is added to a 300 cc FENWAL Transfer Pack using a syringe. Then, 60 cc of the swine plasma is added to the transfer pack. The transfer pack is clamped, all air bubbles removed, and placed in a Stomacher lab blender in which it is blended at normal (or medium) speed for about two minutes. The transfer pack is then removed from the blender, 60 cc of swine red blood cells are added, and the contents mixed by hand kneading for about two minutes, or until the contents appear homogeneous. The final mixture has a red blood cell content of about 30 volume percent and generally is at least within the range of 28-32 volume percent for artificial menses. The amount of egg white is about 40 weight percent.

The nonwoven web material in accordance with one embodiment of this invention comprises a plurality of polymeric fibers comprising one or more treatment chemistries suitable for modifying one or more properties of a high viscoelasticity fluid upon contact with the high viscoelasticity fluid. For many applications, the fiber forming component of the treatment chemistry-containing fiber of this invention will be selected from typical thermoplastic polymers such as polyolefins, including polyethylene, polypropylene, copolymers and blends of these, polyesters, including polyethyleneterephthalate, polyamides, including nylons, and various elastomers and plastomers such as polyurethanes and polyesters as are known to those skilled in the art. Because of the experience with these polymers in forming fibers and because they are readily available at low cost, polyolefins will frequently be the choice for the fiber forming component.

For other applications where melt processes are unsuitable, various polymers that can be dissolved in aqueous or non-aqueous solvents can also serve as fiber forming components. Aqueous based polymer systems such as polyvinyl alcohol, sodium alginate, chitosan, polyvinyl pyrrolidone, hydroxymethyl cellulose and the like or non-aqueous based polymer systems such as polyurethane, ethylene vinyl acetate, acrylic based polymers, chitin, ethylcellulose, polyacryonitrile, and the like can be used.

A wide variety of disposable absorbent articles for collecting bodily fluids, which articles typically comprise nonwoven web materials, are known in the art. Commercial absorbent articles include disposable diapers, sanitary napkins, training pants, and incontinent care pads, wound dressings, and the like. Disposable products of this type include some functional elements for receiving, absorbing, and retaining fluids. Typically, such absorbent articles have an absorbent core containing cellulosic fibers, for example, wood pulp fluff, particles of highly absorbent materials, for example, superabsorbents, and an admixture of cellulosic fibers and superabsorbents. Typically, such articles include a fluid-permeable cover sheet or topsheet which typically faces the body of the user, an absorbent core, and a fluid-impermeable backsheet.

Cover sheet materials are utilized for the transport of bodily fluids into the absorbent core of personal care absorbent articles and, thus, materials used for cover sheet applications must manage distinctly different body excretions, depending upon the application and the product type. Some products must manage fluids, such as urine, while others must manage proteinaceous and viscoelastic fluids, such as menstrual discharge and fecal matter. The management of viscoelastic menstrual discharge by feminine care products such as sanitary pads and napkins is exacerbated due to the variations in composition and rheology over a broad range of elasticity. Fluid management in feminine care applications requires control of absorption of bodily fluids, control of fluid retention in the cover, control of stain size and intensity, control of rewet of fluid back to the surface, and control of the release of fluid to the absorbent core.

Menstrual discharges are composed of blood, vaginal or cervical secretions and endometrial tissues, also called clots. The vaginal secretions are mainly composed of mucins. The proportions of the various components of menstrual fluid vary from woman to woman and from period to period. The proportions of these components also depend upon the age of the woman, the activity of the woman and the method of birth control used by the woman. As a result, the fluid composition can vary from 30 to 70% blood, 10 to 50% cervical secretions, and 0 to 30% endometrial tissues.

Mucin and endometrial tissues are two components that are not easily absorbed into a porous structure made of standard nonwoven materials. These two highly viscous and elastic components are often responsible for cover smearing on a pad and premature leakage (leakage without high content fluid loading in the pad). There are several factors which influence the flow of liquids in fibrous structures including the geometry of the pore structure in the fabrics, the nature of the solid surface (surface energy, surface charge, etc.), the geometry of the solid surface (surface roughness, grooves, etc.), the chemical/physical treatment of the solid surface, and the chemical nature of the fluid.

In accordance with one embodiment of this invention, at least one of the treatment chemistries suitable for use in the nonwoven web materials of this invention is a mucolytic agent. It is believed that the mucolytic agent breaks down some critical disulfide intramolecular and/or intermolecular bonds in the mucus glyco-protein or mucin component of the menstrual fluid, thereby significantly decreasing the viscoelasticity of the mucus. Suitable mucolytic agents comprise a material selected from the group consisting of cysteine, thioglycolates, dithiotriacol, as well as other sulfur-containing thiol materials and combinations and mixtures thereof at a suitable pH.

Personal care absorbent articles in accordance with this invention typically include a fluid pervious cover sheet 5, a fluid impervious back sheet 6 and an absorbent core 7 disposed between the fluid pervious cover sheet and the fluid impervious back sheet as shown in FIG. 1.

Materials used in the production of these personal care absorbent articles include nonwoven web materials which may be produced by any method known to those skilled in the art for producing nonwoven web materials. The fibers from which the nonwoven web materials may be made are produced, for example, by meltblowing or spunbonding processes, including those processes producing multicomponent, biconstituent or polymer blend fibers which are well known in the art. These processes generally use an extruder to supply melted thermoplastic polymer to a spinneret where the polymer is fiberized to yield fibers which may be staple length or longer. The fibers are then drawn, usually pneumatically, and deposited on a moving foraminous mat or belt to form the nonwoven fabric.

Figure 2:
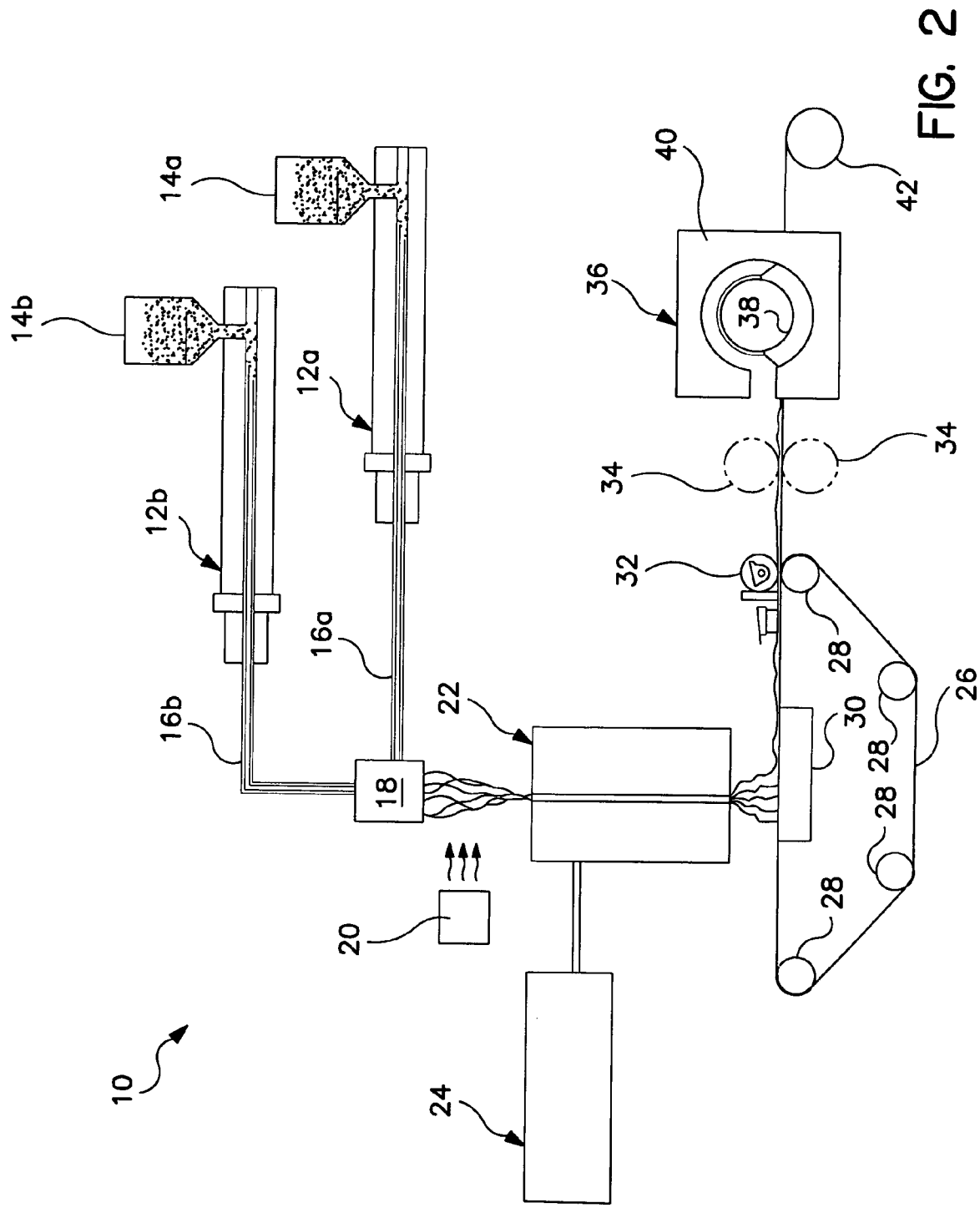
FIG. 2 is a schematic diagram of a method for producing multicomponent fibers of this invention and webs formed therefrom.

Referring, for example, to FIG. 2, a process line 10 for preparing a preferred embodiment of the fibers of this invention is shown. The process line 10 is arranged to produce bicomponent continuous filaments, but it should be understood that the present invention comprehends nonwoven fabrics made with monocomponent agend filaments as well as multicomponent filaments having more than two components. For example, the fiber or fabric of the present invention can be made with filaments having three or four components. The process line 10 includes a pair of extruders 12a and 12b for separately extruding a fiber forming polymer component A as described herein and an agend component B. Polymer component A is fed into the respective extruder 12b from a second hopper 14b. Polymer component A and component B are fed from extruders 12a and 12b through respective polymer conduits 16a and 16b to a spinneret 18. Spinnerets for extruding bicomponent filaments are well known to those of ordinary skill in the art and, thus, are not described here in detail. Generally described, the spinneret 18 includes a housing containing a spin pack which includes a plurality of plates stacked one on top of the other with a pattern of openings arranged to create flow paths for directing components A and B separately through the spinneret. The spinneret 18 has openings arranged in one or more rows. The spinneret openings form a downwardly extending curtain of filaments when the polymers are extruded through the spinneret. For the purposes of this invention, spinneret 18 may be configured to form side-by-side, sheath/core or islands-in-the-sea bicomponent filaments as shown in FIGS. 3A, 3B and 3C as well as modified sheath/core combinations such as shown in FIG. 4.

The process line 10 also includes quench blower 20 positioned adjacent the curtain of filaments extending from the spinneret 18. Air from the quench blower 20 quenches the filaments extending from the spinneret 18. The air can be directed from one side of the filament curtain as shown in FIG. 1, or both sides of the filament curtain. A fiber draw unit or aspirator 22 is positioned below the spinneret 18 and receives the quenched filaments. Fiber draw units or aspirators for use in the process of this invention include a linear fiber aspirator of the type shown in U.S. Pat. No. 3,802,817 and eductive guns of the type shown in U.S. Pat. Nos. 3,692,618 and 3,423,266, the disclosures of which are incorporated herein by reference in their entireties. Generally described, the fiber draw unit 22 includes an elongate vertical passage through which the filaments are drawn by aspirating air entering from the sides of the passage and flowing downwardly through the passage. A heater 24 supplies hot aspirating air to the fiber draw unit 22. The hot aspirating air draws the filaments and ambient air through the fiber draw unit. An endless foraminous forming surface 26 is positioned below the fiber draw unit 22 and receives the continuous filaments from the outlet opening of the fiber draw unit. The forming surface 26 travels around guide rollers 28. A vacuum 30 positioned below the forming surface 26 where the filaments are deposited draws the filaments against the forming surface. The process line 10 further includes a compression roller 32 which, along with the forwardmost of the guide rollers 28, receive the web as the web is drawn off of the forming surface 26. In addition, the process line includes a bonding apparatus such as thermal point bonding rollers 34 (shown in phantom) or through-air bonder 36. Thermal point bonders and through-air bonders are well known to those skilled in the art and are not described here in detail. Generally described, the through-air bonder 36 includes a perforated roller 38, which receives the web, and a hood 40 surrounding the perforated roller. Lastly, the process line includes a winding roll 42 for taking up the finished product.

To operate the process line 10, hoppers 14a and 14b are filled with the respective polymer component A and agend B. Polymer component A and agend B are melted and extruded by the respective extruders 12a and 12b through polymer conduits 16a and 16b and the spinneret 18. Although the temperatures of the molten polymers vary depending on the polymers used, when polypropylene and polyethylene are used as component A and part of agend B respectively, the preferred temperatures of the polymers range from about 370° to about 530° F. and preferably range from about 400° to about 450° F. As the extruded filaments extend below the spinneret 18, a stream of air from quench blower 20 at least partially quenches the filaments and, if desired, may develop a latent helical crimp in the filaments. The quench air preferably flows in a direction substantially perpendicular to the length of the filaments at a temperature of about 45° to about 90° F. and a velocity from about 100 to about 400 feet per minute. After quenching, the filaments are drawn into the vertical passage of the fiber draw unit 22 by a flow of hot air from the heater 24 through the fiber draw unit. The fiber draw unit is preferably positioned 30 to 60 inches below the bottom of the spinneret 18. If crimp is desired, the temperature of the air supplied from the heater 24 is sufficient that, after some cooling due to mixing with cooler ambient air aspirated with the filaments, the air heats the filaments to a temperature required to activate crimp. The temperature required to activate crimp ranges from about 110° F. to a maximum temperature less than the melting point of the lower melting component which for through-air bonded materials is the second component B. The temperature of the air from the heater 24 and thus the temperature to which the filaments are heated can be varied to achieve different levels of crimp. Generally, a higher air temperature produces a higher number of crimps. The ability to control the degree of crimp of the filaments is a particularly advantageous feature because it allows one to change the resulting density, pore size distribution and drape of the fabric by simply adjusting the temperature of the air in the fiber draw unit. The filaments are deposited through the outlet opening of the fiber draw unit 22 onto the traveling forming surface 26. The vacuum 20 draws the filaments against the forming surface 26 to form an unbonded, nonwoven web of continuous filaments. The web is then lightly compressed by the compression roller 32 and then thermal point bonded by rollers 34 or through-air bonded in through-air bonder 36. In the through-air bonder 36, air having a temperature above the melting temperature of component B and below the melting temperature of component A is directed from hood 40, through the web, and into perforated roller 38. The hot air melts the lower melting polymer component of agend B and thereby forms bonds between the bicomponent filaments to integrate the web. When polypropylene and polyethylene are used as polymer component A and part of agend B respectively, the air flowing through the through-air bonder preferably has a temperature in the range of about 230° to about 280° F. and a velocity from about 100 to about 500 feet per minute. The dwell time of the web in the through-air bonder is preferably less than about 6 seconds. It should be understood, however, that the parameters of the through-air bonder depend on factors such as the type of polymers used and the thickness of the web. Lastly, the finished web is wound onto the winding roller 42 and is ready for further treatment or use.

Figure 3A:
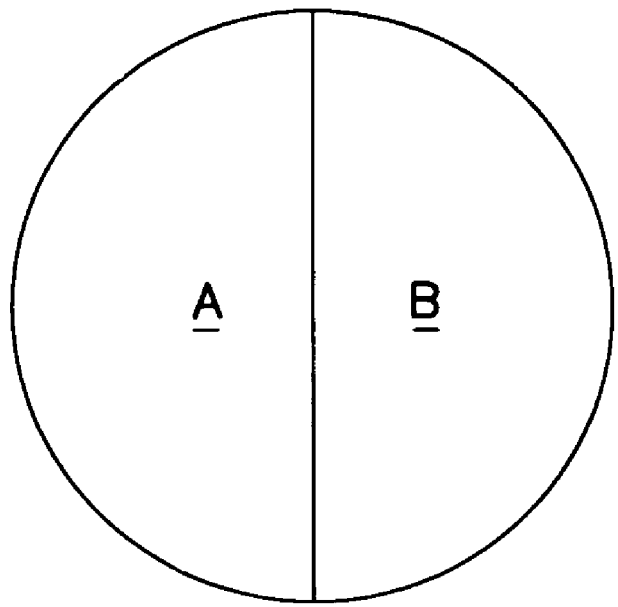
FIGS. 3A, 3B, and 3C are schematic cross-sectional views of side-by-side, sheath/core, and islands-in-the-sea multicomponent fibers of the present invention.
Figure 3B:
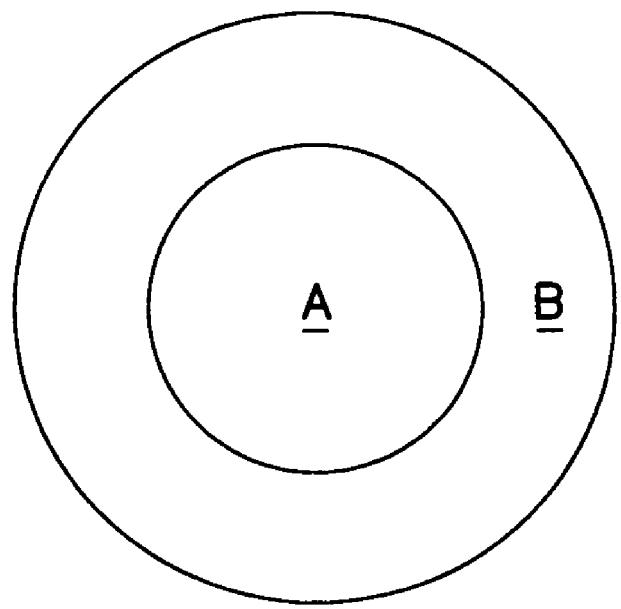
Figure 3C:
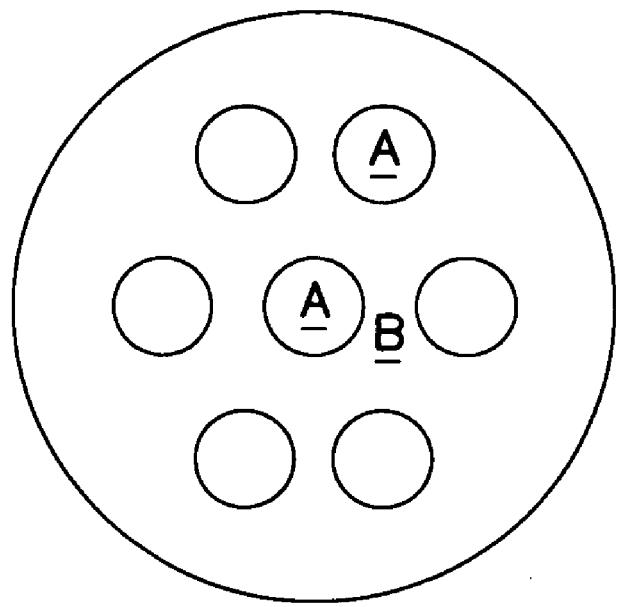
Figure 4:
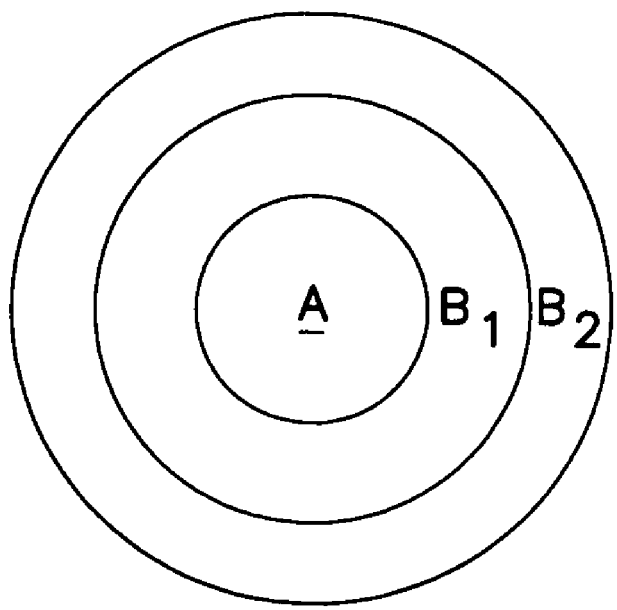
FIG. 4 is a schematic cross-sectional view of an alternative sheath/core multicomponent fiber arrangement in accordance with this invention.

Turning to FIG. 3A, there is shown a side-by-side bicomponent fiber in cross-section showing the distribution of polymer A and agend component B. FIG. 3B is a similar illustration of a sheath/core bicomponent fiber showing a core of polymer component A and a sheath of agend component B. FIG. 3C is a similar illustration of an islands-in-the-sea bicomponent fiber cross-section. As will be appreciated by those skilled in the art, the components need not be circular and, for example, a star-shaped core component can be used to provide increased surface contact between component A and B.

Referring to FIG. 4, there is shown a cross-section of a multicomponent agend fiber of the present invention having three components in concentric arrangement. Component A can be a fiber-forming polymer component as described above, and components $B_1$ and $B_2$ can be different agends. For example, the outer component $B_2$, can be a rapid dispensing agend while middle component $B_1$ can be a slower dispensing agend with the result that an extended dispensing period is provided while, at the same time, providing an immediate dosage.

Alternatively, the nonwoven web may be a bonded carded web. Bonded carded webs are made from staple fibers, which are usually purchased in bales. The bales are placed in a picker, which separates the fibers. Then, the fibers are sent through a combing or carding unit, which further breaks apart and aligns the staple fibers in the machine direction to form a generally machine direction-oriented fibrous nonwoven web. Once the web is formed, it is then bonded by one or more of several known bonding methods, such as powder bonding wherein a powdered adhesive is distributed through the web and then activated by heating the web and adhesive with hot air or some other heat source, pattern bonding wherein heated calender rolls or ultrasonic bonding equipment are used to bond the fibers together, usually in a localized bond pattern, though the web can be bonded across its entire surface, if so desired, and through-air bonding.

As previously stated, menstrual discharges, in particular the mucins and endometrial tissue components thereof are not readily absorbed into a porous structure made of standard nonwoven materials, the result of which is frequently cover smearing and/or premature leakage. Mucins are glycoproteins that form very long chains with many carbohydrate branches. The physical (mechanical entanglement) and chemical (disulfide bonds, ionic reactions, hydrogen bonding) interactions between these long molecular chains result in the formation of very thick, stringy, clear and viscous fluids called cervical mucus.

The use of L-cysteine, like other reducing agents, to reduce disulfide bonds is well known in the literature. A similar compound, N-acetylcysteine, is used as a mucolytic agent to improve clearance in cystic fibrosis and in cough medications. L-cysteine also plays several critical roles in the body. Its more important roles are protecting cells and cellular components against oxidative stress and in detoxification. L-cysteine is a natural sulphur-containing amino acid derivative found naturally in foods and is a powerful antioxidant. These dual properties help repair oxidative damage in the body. This has made this nutrient of special interest to athletes for some time as heavy exercise increases oxidative damage in the body. The most recent research interests are in connection with AIDS and heart disease. For these reasons, L-cysteine is an amino acid used in some food supplements and drugs.

Chemical alteration of the mucus glycoprotein can produce a thinner fluid that can be easily absorbed in porous nonwoven structures. The nonwoven web material in accordance with one embodiment of this invention employs a reducing agent, such as L-cysteine, to break down the long glycoprotein into smaller segments. L-cysteine breaks down critical disulfide bonds in the mucus glycoprotein.

Bench test results indicate that L-cysteine is very effective at thinning the mucus glycoprotein, thereby allowing a rapid intake of very thick mucus-containing fluid. By breaking down some critical disulfide intra and/or intermolecular bonds in the mucus glycoprotein, the L-cysteine significantly decreases the viscoelasticity of the mucus. Thus, the use of this invention can improve the intake rate of menstrual fluid in sanitary pads and tampons, allow the reduced mucus component to wick horizontally instead of staying confined at the insult point, and reduce premature leakage and cover smearing. The use of this invention as a treatment on the cover material and/or on the distribution layer will allow improved absorbency in a feminine care absorbent product. In addition, this invention may be used on a cover material in combination with cover topography and geometry to allow, simultaneously, faster intake rate, better dryness and lower rewet.

One method for determining the effectiveness of a reducing agent in breaking down the disulfide intra and/or intermolecular bonds in the mucus glycoprotein is the use of ANS (8-Anilino-1-naphthalenesulfonate), a substance that fluoresces in a non-aqueous environment but not in an aqueous environment. If the hydrophobic sites of a protein are accessible, then ANS will fluoresce. If the number of hydrophobic sites increases, the fluorescence also increases. An increase of hydrophobic sites indicates that the protein is being broken down. Indirectly, an increase in ANS emission indicates that the mucin protein has been reduced.

The direct addition of 2% by volume L-cysteine to menstrual fluid simulants produces a rapid decrease in the viscoelasticity of the fluid. Tables 1 and 2 hereinbelow show the effects of 2% by volume L-cysteine on both high and low viscoelasticity menses simulants, five (5) minutes after addition, using a Vilastics III rheometer available from Vilastic Scientific, Inc. located in Austin, Tex. operating at a frequency of 0.1 Hz.

TABLE 1

Reduction of Viscoelastic Components of High Viscoelastic Menses Simulant After 5 Minutes Incubation with 2% by Volume L-cysteine

| Sample | Viscosity(Poise) | Elasticity(Poise) |
|---|---|---|
| Control (undiluted) | 0.8 | 0.75 |
| 2% Cysteine | 0.15 | 0.04 |

TABLE 2

Reduction of Viscoelastic Components of Low Viscoelastic Menses Simulant After 5 Minutes Incubation With 2% by Volume L-cysteine

| Sample | Viscosity(Poise) | Elasticity(Poise) |
|---|---|---|
| Control (undiluted) | 0.32 | 0.23 |
| 2% Cysteine | 0.14 | 0.05 |

One problem associated with absorbent articles intended for use in handling fluids comprising blood components such as feminine care products and wound dressings is the tendency of red blood cells to block the pores of the materials used for absorption of fluids in such products. Typical of such porous materials are nonwoven or fibrous web materials. The blockage of the pores of the nonwoven or fibrous web materials by the red blood cells results in a reduction in the fluid intake and the wicking capabilities of such products. In addition, in the case of feminine care products such as sanitary pads and napkins, the blockage of pores of nonwoven materials used therein by red blood cells results in increased staining. In the case of feminine care products comprising superabsorbents, the red blood cells attach themselves to the superabsorbents, resulting in blockage of the superabsorbents and a significant reduction in fluid uptake.

To address these issues, the nonwoven web material in accordance with one embodiment of this invention is treated with a fluid treatment agent whereby red blood cells within a blood-containing fluid absorbed by the absorbent material are agglomerated or lysed. In accordance with one embodiment of this invention, the fluid treatment agent is an agglutinizing (agglomerating) agent which causes the red blood cells in the blood-containing fluid to agglomerate, thereby enabling them to be physically separated from the blood-containing fluid, leaving a fluid that is easier to absorb and less strongly colored. In accordance with another embodiment of this invention, the fluid treatment agent is a cell lysing agent.

In accordance with one embodiment of this invention, the nonwoven web material comprises a gradient of pore sizes produced by layering of nonwoven web layers, each layer of which has an average pore size different from the average pore sizes of other nonwoven web layers, forming a porosity gradient nonwoven web material. When disposed between the cover sheet and the liquid impervious backing material of a personal care absorbent article, the porosity gradient nonwoven web material is disposed such that larger average pore sizes are oriented toward the cover sheet and the average pore size of the nonwoven web material decreases in the direction of the liquid impervious backing material. As a result, the porosity gradient nonwoven web material acts as a "depth filter" wherein the agglomerated red blood cells become trapped within the larger size pores of the porosity gradient nonwoven web material. However, care must be taken in selecting the pore size gradient to insure that the fluid separated from the agglomerated red blood cells is still able to pass by trapped particles or clumps of red blood cells, thereby enabling further distribution of the fluid within the personal care absorbent article as desired, for example, to a superabsorbent.

One of the benefits of this invention derives from the fact that the red blood cells of a blood-containing fluid, having come into contact with the fluid treatment agent, are no longer able to block the flow of fluids into the superabsorbents that may be present. This is particularly surprising in the case where the red blood cells are lysed because, unlike agglomerated cells which may become trapped within the pores of the nonwoven material, resulting in their separation from the remaining fluid components, i.e. plasma, the components of the lysed cells remain in the fluid but apparently are no longer able to attach themselves to the superabsorbents.

To provide separation of the red blood cells from the blood-containing fluids absorbed into the personal care absorbent article in accordance with one embodiment of this invention, the porous nonwoven web material is treated with a fluid treatment agent which is an agglutinizing agent which causes the red blood cells to clump upon coming into contact with the agglomerating agent. Suitable agglutinizing fluid treatment agents for use in the personal care absorbent article of this invention include, but are not limited to, antibodies, polycationic materials, that is highly positively charged polymers, and tri-block copolymers of polypropylene oxide and polyethylene oxide. One particularly suitable tri-block copolymer goes under the commercial name of PLURONIC® F-98 available from BASF (Germany) and constitutes a particularly preferred embodiment of this invention. PLURONIC F-98 is a tri-block copolymer surfactant of 80% by weight polyethylene oxide and 20% by weight polypropylene oxide having a molecular weight of about 9000.

Investigations which we have conducted have shown that greater than about a 1% by weight PLURONIC F-98 solution is required to agglomerate red blood cells in blood and menses. In accordance with a particularly preferred embodiment of this invention, the agglomerating fluid treatment agent is a 2% by weight solution of PLURONIC F-98.

EXAMPLES

One gram of a 20% solution of PLURONIC® F-98 was mixed with blood and 3 grams of the resulting mixture were applied to a piece of polyethylene film. After five minutes, the blood was drained off. Observation of the "treated" blood under a microscope revealed that the red blood cells had agglomerated without lysing.

As a result of treatment of the porous nonwoven web material with an agglomerating fluid treatment agent, the red blood cells clump together and are "filtered" out of the menses or blood as a result of being trapped in the pores of the nonwoven web material. In accordance with one preferred embodiment of this invention, the nonwoven web material comprises a porosity gradient which acts as a "depth filter". The remaining fluid, without the red blood cells, is less colored, as a result of which any leakage which may occur is not as easily detected. In addition, the uptake of the menses by the nonwoven web material and the superabsorbents which may be present without the red blood cells is improved compared to menses in which the red blood cells are present because the red blood cells are no longer available for clogging passages in the nonwoven web material (wicking material) and superabsorbents. Finally, in the absence of red blood cells, the menses exhibits reduced viscoelastic properties, that is improved fluid intake, distribution and absorption properties.

In accordance with one preferred embodiment of this invention, the fluid treatment agent applied to the nonwoven web material is a red blood cell lysing agent. We have found that at least some lysing agents in accordance with this invention are effective in their ability to lyse red blood cells at concentrations as low as 0.1% by weight. Suitable lysing agents for use in the personal care absorbent articles of this invention include GLUCOPON 220, an octylpolyglycoside available from Henkel Corporation, Ambler, Pa., MASIL® SF-19, an alkoxylated polysiloxane available from PPG Industries, Inc., Specialty Chemicals Division, Gurnee, Ill., nonionic surfactant LAURETH 7, an alkoxylated alcohol available from Heterene, Inc., Paterson, N.J., nonionic LAURETH 4, an alkoxylated alcohol available from Heterene, Inc., nonionic PPG 5-Laureth 5, an alkoxylated alcohol available from Henkel Corporation, amphoteric surfactant DERIPHAT 160S, an alkyl-substituted amino acid available from Henkel/Cospha, Ambler, Pa., anionic surfactant sodium laurel sulfate, an alkyl sulfate available from Henkel, amphoteric MACKAM 15-L, an alkyl substituted amino acid available from McIntyre Group, University Park, Ill., anionic MACKANATE LM-40, a sulfosuccinate available from McIntyre Group, anionic STANDOPOL SH124-3, a sulfosuccinate available from Henkel/Cospha, and anionic HAMPOSYL L-30, a sarcosinate available from Hampshire Chemical, Lexington, Mass.

In accordance with a particularly preferred embodiment of this invention, the red blood cell lysing agent is a water soluble saponin, a high molecular weight glycoside comprising a sugar part linked to a triterpene or steroid aglycone. A suitable saponin produced from quillaja bark is available from Sigma Chemical Company, St. Louis, Mo.

The leaking of even small amounts of menses is unacceptable in a femcare product such as a pad or tampon because the menses is intensely colored and difficult to remove once it causes a stain. It is, thus, an important goal to reduce leakage as much as possible. One method of reducing leakage would be to modify the menses so that it will not flow. This may be accomplished by increasing the viscosity and elasticity of the menses fluid. Two types of chemical additives have been shown to produce this effect. Both types of agents interact with the fluid to produce a gel. Thickeners interact with the water in the menses and then interact with themselves to gel the menses. Cross-linking gels gel the solution by cross-linking the protein molecules.

The mechanism of certain thickeners is to expose the fluid to be thickened to particles of the thickening agent and allow them to swell and bind to each other, thereby thickening and, eventually, gelling the fluid. In accordance with one embodiment of this invention, soluble fibers or other similar particles are mixed into a target fluid. Soluble fiber particles can be found in products like METAMUCIL® and CITRUCEL® among others. Additionally, they are an agricultural product used in horse and human food. More particularly, 10% (by mass) Metamucil is mixed with water, creating an emulsion of psyllium husk particles (the active ingredient) within the water, eventually creating a gel. Microscopy indicates that fibrils from a central crystal expand, or "bloom", out into the fluid and entrap the water. Over time, the fibrils begin to lose their distinct boundaries and bind to adjacent fibrils. This binding is not permanent, as the emulsion will reconfigure if more fluid is added and sufficient mixing occurs. In another example, 10% (by mass) Metamucil is mixed with menses simulant. The mechanism and effects appear to be the same as before except that they occur more rapidly. When applied to a rayon/cotton gauze pad, the gelled simulant only minimally wetted the pad. There was very little seepage through the thin spunlace, indicating good lock-up of the fluid. In yet another successful example, 10% (by mass) Metamucil was mixed with 0.2% saline and blood. The only effect observed with more viscoelastic fluids was that gelling occurs more rapidly. It will be appreciated that the use of thickening particles differs from the use of superabsorbents in absorbent articles in that they not only incorporate fluid into their structures, but they also bind to adjacent particles to form a bulk gel. In addition, they do not dissolve in solutions and they do not rely upon ionic bonding to generate a gel network as is the case with, for example, celquat.

As previously stated, absorbent articles in accordance with this invention typically comprise a fluid permeable cover, a fluid impermeable backsheet and an absorbent core disposed between the fluid permeable cover and the fluid impermeable backsheet. Each of these components may comprise one or a plurality of material layers. Thickening and gelling agents employed in accordance with this invention may be distributed throughout one or more layers of the absorbent article, or they may be distributed within a portion of one or more layers of the absorbent article so as to refine the aspects of control imparted to the absorbent article by the thickening and gelling agents. More particularly, the thickening and gelling agents may be located within a single component absorbent core, among different components within a multicomponent absorbent core, or between different components of a multicomponent absorbent core to modify their effect on overall fluid handling within the article.

Incorporation of thickening and gelling agents into absorbent articles for the purpose of managing the flow of viscoelastic fluids within the absorbent articles may be achieved in a variety of ways. They may be incorporated into the absorbent article on their own or by means of airlaid, airformed, wetlaid, absorbent laminates, or nonwoven materials, such as spunbond, meltblown, coform and through-air bonded carded webs. In accordance with one embodiment of this invention, the thickening and/or gelling agents are mixed at a prescribed concentration into the materials, such as woven and nonwoven materials employed in the absorbent articles, during the manufacturing process. Alternatively or additionally, the thickening and gelling agents may be added directly into the product in the fluff forming unit or as an adhesively laminated layer during product production. Because the thickening and gelling agents are soluble in water, solutions can be used to coat any particular part of the product. Coatings applied to the surface of the absorbent article may be used to improve absorbency of the article.

Figure 5:
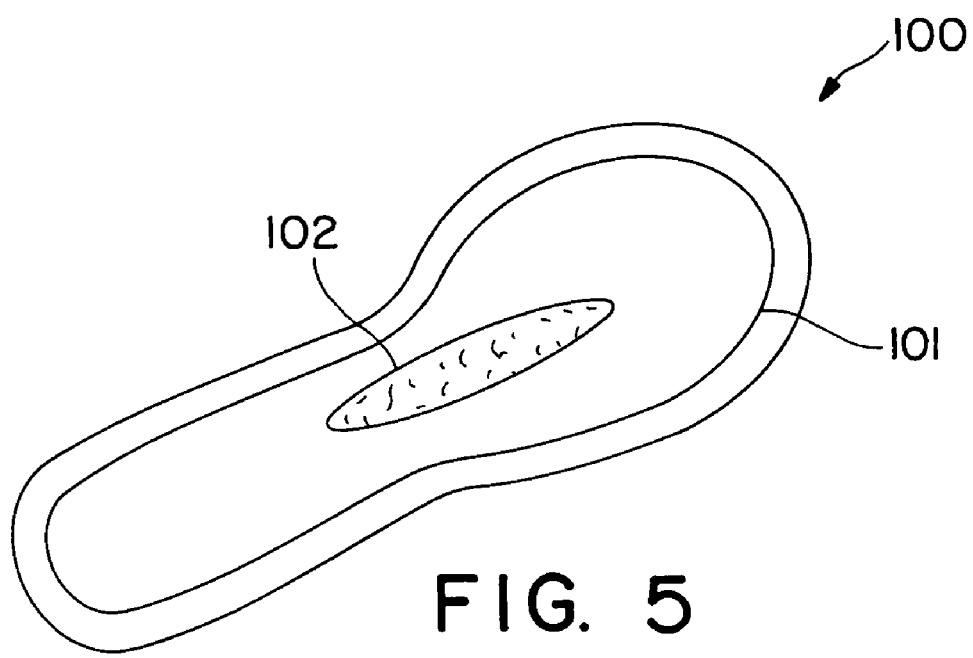
FIG. 5 is a diagram showing disposition of a gelling agent within the central region of an absorbent article.
Figure 6:
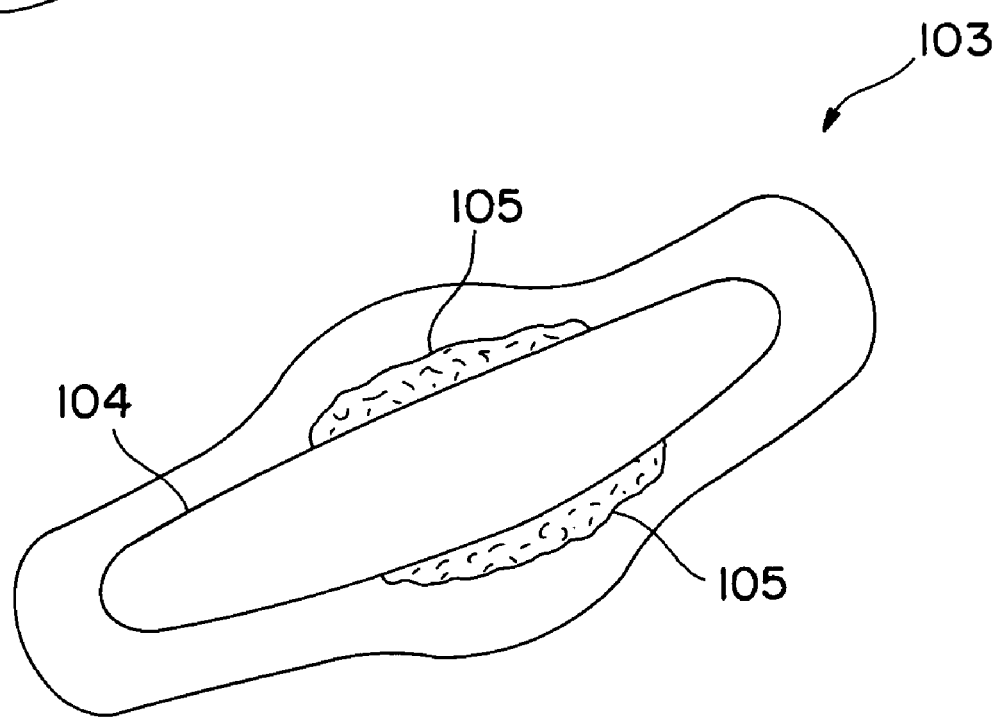
FIG. 6 is a diagram showing disposition of a gelling agent alongside or within the edges of the absorbent core of an absorbent article.
Figure 7:
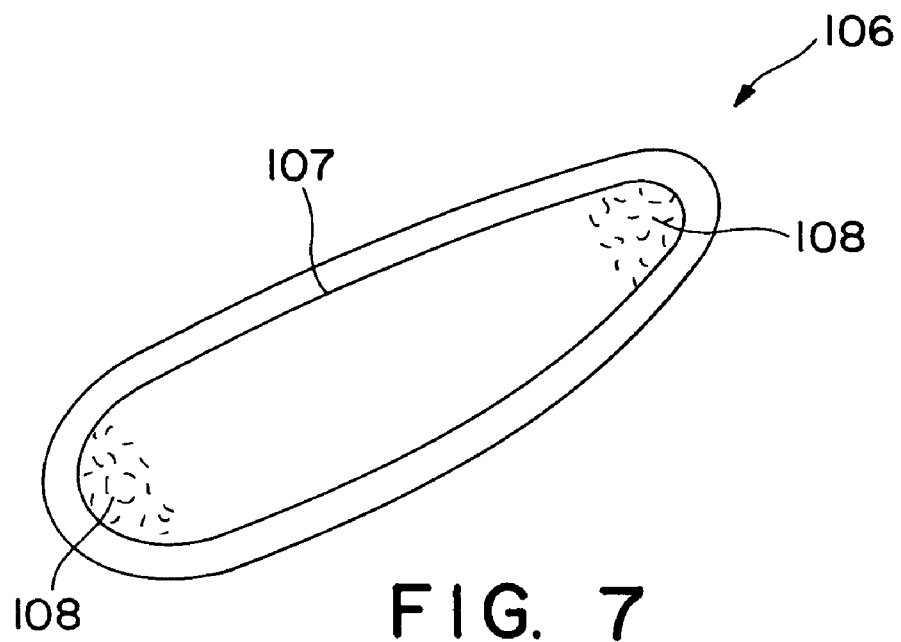
FIG. 7 is a diagram showing disposition of a gelling agent alongside or within the ends of the absorbent core of an absorbent article.
Figure 8:
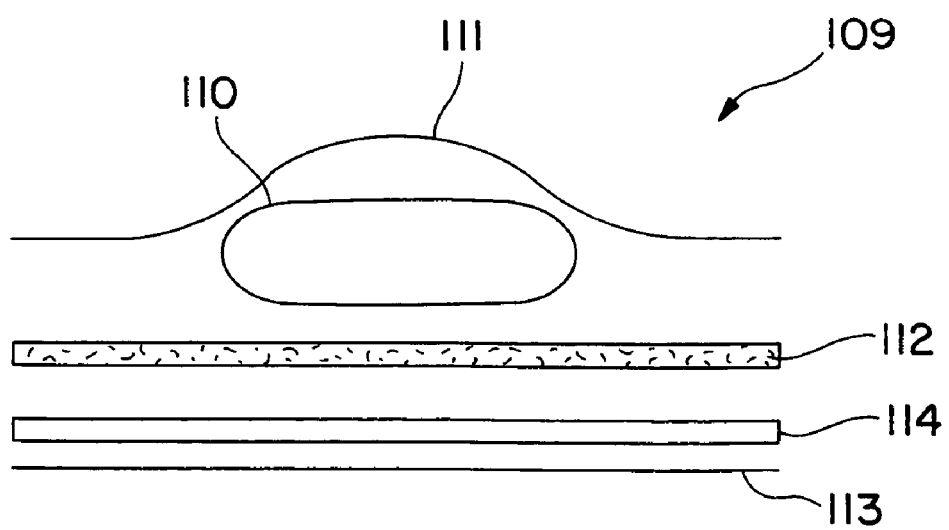
FIG. 8 is a diagram showing disposition of gelling agents in a central region or within a relatively open, low basis weight component of an absorbent article.

In accordance with one embodiment of this invention, the gelling and thickening agents are applied in a pattern within a nonwoven material, thereby enabling two types of fluid control within the component. In accordance with another embodiment of this invention, the gelling and thickening agents are employed in specific areas of the absorbent article so as to restrict fluid movement within the article. As shown in FIG. 5, the gelling agent 102 may be disposed in a central location of the absorbent 101 of a feminine care product 100 to improve overall containment of menses, and therefore capacity, in that region of the product. As shown in FIG. 6, a gelling agent 105 may be disposed alongside or within the edges of the absorbent core 104 of a feminine care absorbent article 103, thereby gelling menses that is insulted or wicked into this area. In this manner, an effective barrier to fluid flow beyond the edge of the absorbent is created. Similarly, as shown in FIG. 7, gelling agents 108 may be located alongside or within the end of the absorbent core 107 of an absorbent article 106 to create an effective fluid barrier at the ends of the absorbent core. The gelling agent may be varied in the z-direction of the product. The gelling agent may also be disposed only in the cover or upper airlaid layer (cover-facing portion of the absorbent core) to control stain size or in the middle or lower layers of a multi-layer absorbent to impart the barrier function for leakage prevention. Other types of patterning, such as the application to either the cover or the absorbent of the thickening or gelling agent in a checkerboard pattern, could be employed whereby fluid encountering the areas that contain the thickening or gelling agent would start to gel while still permitting the fluid flow through the areas that did not contain the gelling agent. FIG. 8 shows an absorbent article 109 having a cover 111, an absorbent 110, an internal partial barrier 112, a baffle 114 and a backsheet 113 with placement of gelling agents 112 in a central region or within a relatively open, low basis weight component of the absorbent article 109 to eliminate or slow wicking of fluid to a component disposed therebelow. By slowing the movement of the fluid to the bottom layer, the integrity of the bottom layer is preserved and overall product shape is maintained throughout the wear time of the product.

The gelling or thickening agents may be adhered or bonded to a breathable baffle to prevent transfer of evaporated fluid through the cover. This would minimize condensation on the outside of the baffle which, in turn, would reduce dampness perception to the wearer. Similarly, the back film baffle could be coated with gelling or thickening agents to localize the menses at the very bottom of the product. Various parts of the cover could be coated to prevent the movement of menses through the sides of the cover and thereby centralize the menses to the center of the pad. Similarly, the covering of side wings could also be coated to prevent fluid from smearing off the surface of the wings onto undergarments or skin. For all executions for placement of gelling or thickening agents into the absorbent, the agents could be added and fiber or bulk removed to provide equal fluid capacity in a thinner product execution. Such a thinner product would provide greater comfort and improved fit to the wearer.

Protein cross-linking agents gel the fluid by producing a matrix of protein and cationic polymers that is hydrated. We have found that all cationic polymers do not work equally well. Suitable ionically cross-linking gelling agents for use in the personal care articles of this invention include celquat (National Starch and Chemical Company), UCARE polymers (Amercol division of Union Carbide) and chitosan (Vanson), which are mixed with a binder such as KYMENE® 557LX, a liquid binder available from Fibervisions LLC and a non-debonded pulp (NB416) available from Weyerhaeuser Corporation of Tacoma, Wash. Other suitable liquid binders include ethylene vinyl acetate emulsion polymers sold by National Starch and Chemical Company (Bridgewater, N.J.) under the tradename Dur-O-Set® ELITE® series (including ELITE® 33 and ELITE® 22). Air Products Polymers and Chemicals sells other suitable binder fibers under the name AIRFLEX®. The celquat polymers appear to work the best and, thus, are preferred. These include the L-200, H-100, SC-230 and SC-240, available from National Starch and Chemical Company. In each case, a polymer of glucose is connected with β(1→4) linkages (it has been shown that α(1→4) linkages have much lower effectiveness). This is taken to mean that a relatively stiff polyglycan backbone produces increased effectiveness. It is apparent that other polyglycan structures that have reduced rotation, and are therefore stiff, would also be effective; or for that matter any polymer with reduced freedom of movement would suffice. Whatever the case may be, the stiff backbone has positive charges at intervals along the backbone. These positive charges come from ammonium ions in the case of Celquat, UCARE and chitosan salts, but could, in principle, be produced from other substituents as well.

In accordance with one embodiment of this invention, a superabsorbent polymer such as FAVOR 880 ® available from Stockhausen, Inc. 2401 Doyle Street Greensboro, N.C. 27406 is mixed with the gelling agent (e.g. Celquat, UCARE polymer or chitosan). The result is an increase in the absorptive properties of fluff or airlaid composites when insulted by simulant. As shown in Table 3, fluff or airlaid structures containing gelling agents, such as Celquat L-200 or UCARE JR-30M, superabsorbent Favor 880 in a fluff (NB416) or airlaid NB416with T-255 fibers) show an increase in absorbency over that of either superabsorbent or gelling agent used separately. Absorbency is the ability of the fabric to hold fluid under a centrifugal load. The absorbency is measured by saturating a 2-inch diameter fabric sample with 25 ml of simulant for 30 minutes, letting it drain for 5 minutes and then applying a centrifugal load of 1200 rpm for 3 minutes and then measuring the weight gain.

TABLE 3

| Composition | | | | Centrifuge |
|---|---|---|---|---|
| % NB-416 Fluff | % T-255 Binder | % Favor 880 | % Celquat L-200 | Capacity (g/g) |
| 90 | 10 | | | 2.61 |
| 80 | 10 | 10 | | 3.76 |
| 87 | 10 | | 3 | 3.66 |
| 77 | 10 | 10 | 3 | 5.13 |
| 80 | 10 | | 10 | 4.86 |
| 70 | 10 | 10 | 10 | 5.40 |

For a nonwoven web material having a basis weight of about 150 gsm, a typical composition for incorporation into the nonwoven web material in accordance with one embodiment of this invention comprises, in % by weight of the composition, in the range of about 60% to about 87% NB416, in the range of about 3% to about 10% celquat, in the range of about 0% to 10% Favor 880, and about 10% of a binder.

Having described the various treatment chemistries suitable for use in the nonwoven web materials of this invention, it will be apparent to those skilled in the art that there exists a variety of embodiments of this invention which may find application in personal care articles. For example, distribution of the treatment chemistry within the nonwoven web material may be uniform. Alternatively, the treatment chemistry may be distributed within specific zones of the nonwoven web material. Yet a further alternative may be the distribution of the treatment chemistry in the nonwoven web material in a manner whereby a gradient is established within nonwoven web material. The nonwoven material may be a multilayer nonwoven material or laminate in which the desired treatment chemistry is distributed in fewer than all of the layers in a uniform manner, in zones or as a gradient. And, it will also be apparent that combinations of treatment chemistries may be employed in the nonwoven web materials of this invention based upon the particular application of the material. Without intending to limit the scope of this invention, all of these embodiments are deemed to be within the scope of this invention.

We claim:

1. A method for treating a viscoelastic proteinaceous fluid, whereby management of said viscoelastic fluid by a personal care absorbent article is improved, comprising the steps of:

treating at least one portion of said personal care absorbent article with at least one treatment chemistry selected from the group consisting of water-soluble gelling agents which crosslink protein, thickening agents, plasma precipitators and combinations thereof; and contacting said at least one portion of said personal care absorbent article with said viscoelastic fluid, thereby one of altering at least one property of said viscoelastic fluid and altering an interaction between said absorbent article and said viscoelastic fluid;

wherein said personal care absorbent article includes a fluid pervious polyolefin cover sheet, a fluid impervious backsheet, and an absorbent core between them, said cover sheet, said backsheet and said absorbent core comprise at least one nonwoven web material comprising a plurality of polymeric fibers having said at least one treatment chemistry disposed within said plurality of polymeric fibers, and at least a portion of said polymeric fibers are bicomponent fibers having said at least one treatment chemistry disposed within one segment of said bicomponent fibers.

2. A method in accordance with claim 1, wherein said viscoelastic fluid is menses.

3. A method in accordance with claim 1, wherein said at least one treatment chemistry is in a form of solid particles.

4. A method in accordance with claim 1, wherein said at least one treatment chemistry is uniformly dispersed on said portion of at least one of a surface and an interior of said absorbent article.

5. A method in accordance with claim 1, wherein said at least one treatment chemistry is disposed along a peripheral region of said absorbent core.

6. A method in accordance with claim 1, wherein said at least one treatment chemistry is dispersed within said at least one of said cover sheet, said backsheet and said absorbent core so as to form a gradient therein.

7. A method in accordance with claim 1, wherein said at least one treatment chemistry comprises the water-soluble gelling agent and a superabsorbent is disposed in said absorbent core.

8. A method in accordance with claim 1, wherein said absorbent article comprises a nonwoven web material selected from the group consisting of airlaid, coform, spunbond, meltblown, bonded carded web, non-bonded pulp, bonded pulp, fibrous webs and combinations thereof.

9. A method in accordance with claim 1, wherein said nonwoven web material is a laminate.

10. A method in accordance with claim 5, wherein said at least one treatment chemistry is applied to at least one of opposed edges, opposed ends and a center region of said absorbent core.

11. A method in accordance with claim 1, wherein said personal care absorbent article comprises at least two opposed side wings to which said at least one treatment chemistry is applied.

12. In an absorbent article comprising an absorbent layer having a first surface and a second surface, a fluid permeable cover disposed adjacent said first surface, a fluid impervious baffle disposed adjacent said second surface, the improvement comprising:
  at least one treatment chemistry selected from the group consisting of water-soluble gelling agents which crosslink protein, thickening agents, agglutinizing agents, plasma precipitators, mucolytic agents, lysing agents and combinations thereof disposed at least one of on or within at least a portion of said absorbent layer; and opposed side wings to which the treatment chemistry is applied.

13. An absorbent article in accordance with claim 12 further comprising a superabsorbent disposed within said absorbent layer.

14. An absorbent article in accordance with claim 13, wherein said treatment chemistry comprises the water-soluble gelling agent.

15. An absorbent article in accordance with claim 12 further comprising at least one material selected from the group consisting of airlaid, airformed, wetlaid, absorbent laminates, nonwovens and combinations thereof.

16. An absorbent article in accordance with claim 12, wherein said at least one treatment chemistry is disposed on at least a portion of one of said fluid permeable cover and said fluid impervious baffle.

17. An absorbent article in accordance with claim 12, wherein said at least one treatment chemistry is disposed on at least one of a peripheral region and a center region of said absorbent layer.

18. An absorbent article in accordance with claim 17, wherein said peripheral region comprises opposed edges and opposed ends of said absorbent layer.

19. An absorbent article in accordance with claim 12, wherein said at least one treatment chemistry is one of said water-soluble gelling agent and said thickening agent.

20. A personal care absorbent article comprising: a fluid pervious polyolefin cover sheet, a fluid impervious backsheet, and an absorbent core between them;
  at least one of the cover sheet, backsheet and absorbent core including a nonwoven material treated with a treatment chemistry selected from the group consisting of water-soluble polyglycan gelling agents which crosslink protein, thickening agents, plasma precipitators and combinations thereof
  wherein said treatment chemistry is disposed along a peripheral region of said absorbent core and not a center of said absorbent core.

21. An absorbent article in accordance with claim 20, wherein at least one superabsorbent is disposed within said nonwoven material.

22. An absorbent article in accordance with claim 20, wherein said treatment chemistry comprises the water-soluble gelling agent.

23. An absorbent article in accordance with claim 20, wherein said treatment chemistry is disposed within a plurality of polymeric fibers comprising said nonwoven material.

24. An absorbent article in accordance with claim 20, wherein said nonwoven material is selected from the group consisting of airlaid, spunbond, meltblown, bonded carded, non-bonded pulp, bonded pulp and combinations thereof.

25. An absorbent article in accordance with claim 20, wherein said nonwoven material comprises a plurality of nonwoven layers.

26. An absorbent article in accordance with claim 25, wherein said at least one treatment chemistry is dispersed at least one of on and in less than all of said plurality of nonwoven layers.

27. An absorbent article in accordance with claim 20, wherein said at least one treatment chemistry is dispersed non-homogeneously within said nonwoven material.

28. An absorbent article in accordance with claim 20, wherein said at least one treatment chemistry is disposed on a surface of at least a portion of a plurality of polymeric fibers of said nonwoven material.

29. An absorbent article in accordance with claim 20, wherein said nonwoven material comprises a plurality of bicomponent polymeric fibers and said at least one treatment chemistry is disposed in only one segment of said bicomponent polymeric fibers.

* * * * *